United States Patent
Selvaraj et al.

(10) Patent No.: US 10,373,714 B1
(45) Date of Patent: Aug. 6, 2019

(54) DETERMINATION OF BED-TIME DURATION USING WEARABLE SENSORS

(71) Applicant: Vital Connect, Inc., Campbell, CA (US)

(72) Inventors: Nandakumar Selvaraj, San Jose, CA (US); Toai Doan, Saratoga, CA (US)

(73) Assignee: Vital Connect, Inc., San Jose, CA (US)

( * ) Notice: Subject to any disclaimer, the term of this patent is extended or adjusted under 35 U.S.C. 154(b) by 1112 days.

(21) Appl. No.: 14/606,897

(22) Filed: Jan. 27, 2015

Related U.S. Application Data (63) Continuation-in-part of application No. 13/941,387, filed on Jul. 12, 2013, now Pat. No. 9,471,541.

(51) Int. Cl.
| | |
|---|---|
| *A61B 5/00* | (2006.01) |
| *G16H 40/63* | (2018.01) |
| *G01B 21/22* | (2006.01) |
| *A61B 5/11* | (2006.01) |

(52) U.S. Cl.
CPC ............ *G16H 40/63* (2018.01); *A61B 5/1115* (2013.01); *A61B 5/1116* (2013.01); *A61B 5/1118* (2013.01); *A61B 5/1121* (2013.01); *A61B 5/6801* (2013.01); *A61B 5/7282* (2013.01); *G01B 21/22* (2013.01)

(58) Field of Classification Search
USPC ....................................................... 702/176
See application file for complete search history.

(56) References Cited

U.S. PATENT DOCUMENTS

| | | | |
|---|---|---|---|
| 6,044,297 A | 3/2000 | Sheldon et al. | |
| 6,494,850 B1 | 12/2002 | Kitadou | |
| 6,695,799 B2 | 2/2004 | Kitadou | |
| 9,028,407 B1 | 5/2015 | Bennett-Guerrero | |
| 9,035,794 B2 | 5/2015 | Narasimhan | |
| 9,471,541 B1 | 10/2016 | Chan | |
| 2002/0183667 A1 | 12/2002 | Kitadou | |
| 2005/0115561 A1* | 6/2005 | Stahmann | A61B 5/0031 128/200.24 |
| 2006/0293604 A1* | 12/2006 | Carlson | A61B 5/0205 600/509 |
| 2007/0032733 A1 | 2/2007 | Burton | |
| 2007/0115277 A1 | 5/2007 | Wang et al. | |
| 2007/0123758 A1* | 5/2007 | Miesel | A61B 5/0205 600/301 |
| 2008/0071326 A1* | 3/2008 | Heruth | A61B 5/0205 607/59 |

(Continued)

*Primary Examiner* — Paul D Lee
(74) *Attorney, Agent, or Firm* — Brundidge & Stanger, P.C.

(57) ABSTRACT

A method and system for automatically determining bed-time periods are disclosed. The method comprises detecting at least one physiological signal, determining a posture angle and an activity level using the at least one detected physiological signal, and determining a bed-time period using both the posture angle and the activity level. The system includes at least one sensor to detect a plurality of physiological signals, a processor coupled to the at least one sensor, and a memory device coupled to the processor, wherein the memory device includes an application that, when executed by the processor, causes the processor to detect a posture angle using at least one of the plurality of detected physiological signals and to determine a bed-time period using both the posture angle and the activity level.

15 Claims, 6 Drawing Sheets

(56) References Cited

U.S. PATENT DOCUMENTS

| | | |
|---|---|---|
| 2008/0300449 A1* | 12/2008 | Gerber ............... A61N 1/36007 |
| | | 600/30 |
| 2010/0010583 A1 | 1/2010 | Panken et al. |
| 2010/0298655 A1 | 11/2010 | McCombie et al. |
| 2011/0172927 A1 | 7/2011 | Sahasrabudhe et al. |
| 2011/0201969 A1 | 8/2011 | Hatlestad et al. |
| 2011/0241656 A1 | 10/2011 | Piemonte et al. |
| 2012/0101411 A1 | 4/2012 | Hausdorff et al. |
| 2012/0108915 A1* | 5/2012 | Corbucci ........... A61B 5/02028 |
| | | 600/301 |
| 2012/0203487 A1 | 8/2012 | Johnson et al. |
| 2013/0090881 A1 | 4/2013 | Janardhanan |
| 2013/0274830 A1 | 10/2013 | Skelton |
| 2014/0015687 A1 | 1/2014 | Narasimhan |
| 2014/0019080 A1 | 1/2014 | Chan |
| 2014/0066816 A1 | 3/2014 | McNames |
| 2014/0128778 A1 | 5/2014 | Chan |
| 2014/0148867 A1* | 5/2014 | Zielinski ............. A61B 5/0537 |
| | | 607/3 |
| 2014/0335490 A1* | 11/2014 | Baarman ................ A61B 5/002 |
| | | 434/236 |
| 2015/0190086 A1 | 7/2015 | Chan |
| 2015/0257654 A1 | 9/2015 | Bennett-Guerrero |

\* cited by examiner

DETERMINATION OF BED-TIME DURATION USING WEARABLE SENSORS

CROSS-REFERENCE TO RELATED APPLICATIONS

This application is a continuation-in-part of U.S. patent application Ser. No. 13/941,387, filed on Jul. 12, 2013, entitled "DETERMINING A TIME PERIOD A PERSON IS IN BED," which is incorporated herein by reference in its entirety.

FIELD OF THE INVENTION

The present invention relates to wearable sensor devices, and more particularly, to automatically determining bed-entry events, bed-exit events, and the derived bed-time periods (e.g., time between bed-entry and bed-exit events) using wearable sensor devices.

BACKGROUND

Bed-time/sleep duration has been progressively shortened over the recent decades due to various reasons including work, cultural, social life, and academic burden. Chronic sleep insufficiency or sleep loss is one of the leading causes for emotional/behavioral issues, functional/cognitive impairment and obesity, not only among adolescents but also children. In addition to the sleep duration, sleep timings such bed-entry and bed-exit are shown to be strong predictors of activity profile, behavioral disorders, and obesity. Therefore, accurate monitoring of sleep timings and duration is useful for various applications including sleep analysis, assessment of wellness/overall health of an individual, and bed-exit alarms.

Conventionally, sleep duration/timing is monitored using sensors including pressure, force, temperature, and movement mounted on the bed. These commonly used technologies are limited by their expense, mostly wired integrated systems, periodic maintenance requirements, exposure to fluids in incontinence patients or by accidents, decreased accuracy in under/normal weight people, and correct and precise sensor placement requirements. Therefore, there is a strong need for a wearable biosensor solution that overcomes the aforementioned issues. The present invention addresses such a need.

SUMMARY OF THE INVENTION

A method and system for automatically determining bed-time periods are disclosed. In a first aspect, the method comprises detecting at least one physiological signal, determining a posture angle and an activity level using the at least one detected physiological signal, and determining a bed-time period using both the posture angle and the activity level.

In a second aspect, the system includes at least one sensor to detect a plurality of physiological signals, a processor coupled to the at least one sensor, and a memory device coupled to the processor, wherein the memory device includes an application that, when executed by the processor, causes the processor to detect a posture angle and an activity level using at least one of the plurality of detected physiological signals and to determine a bed-time period using both the posture angle and the activity level.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

The present invention relates to wearable sensor devices, and more particularly, to automatically determining bed-entry events, bed-exit events, and the derived bed-time periods (e.g., time between bed-entry and bed-exit events) using wearable sensor devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Sleep routines are strong predictors of overall health and wellness. Sleep deficiency is a major problem of the modernized world and major risk factor for metabolic/behavioral disorders, cardiovascular diseases and obesity. Therefore, automated monitoring of bed-entry and bed-exit events and sleep duration can be very valuable for a variety of applications and individuals.

The applications that can benefit from the automated monitoring of bed-entry/exit data include but are not limited to athletic training, automated sleep analysis including sleep stages and quality of sleep, automated screening of sleep apnea syndrome (SAS), assessment of circadian rhythms, chronic stress, and bed routines, weight loss management, and the generation of alerts/alarms to care providers. In addition to the general population, there are specific groups of individuals that can benefit from the automated monitoring of bed-entry/exit data include but are not limited to discharged individuals from hospitals who might require close watch to render support and care, individuals with disabilities or limited mobility, athletes, and elderly individuals/subjects that are in home, hospital, and home care settings.

The amount of time a person is in bed ("bed-time period") can be determined by utilizing posture angles derived from human body acceleration signals (as described in U.S. patent application Ser. No. 13/941,387, filed on Jul. 12, 2013, entitled "DETERMINING A TIME PERIOD A PERSON IS IN BED," which is incorporated herein by reference in its entirety). Utilizing posture angles alone may split a single bed-time period epoch into more than one bed-time period epoch and lead to false positive and false negative bed-time periods. The inaccuracies of bed-time algorithms based on only the posture angles could be due to the inherent limitations of the posture angle variability across demographics. Tosses and turns or sleeping with too many pillows may cause the magnitude of the posture angle to reflect non-supine postures and often result in very unusual sleeping postures. If these unusual sleeping postures occur intermittently or over a prolonged duration, algorithms based on only the posture angle might trigger inaccurate onset and termination of the bed-time period and lead to one or more false positive and false negative bed-time period epochs. A bed-time period is the time duration of a bed-time epoch.

A method and system in accordance with the present invention provides a wireless, portable, and wearable sensor device ("wearable device") that can be in a patch form factor and that is attached to a user (patient) at a plurality of locations including but not limited to chest, arm, and forehead to automatically and continuously detect when the user enters the bed ("bed-entry") and when the user exits the bed ("bed-exit") and determine bed-time periods (the time difference between each bed-entry and bed-exit). The wearable device utilizes an embedded algorithmic process comprising an algorithm to provide more accurate assessment of bed-entry and bed-exit time events while eliminating the aforementioned false positives and false negatives that may result from a posture angle only approach. The method and system provide for automatically determining bed-time periods/sleep durations.

In one embodiment, the algorithm combines not only posture angle calculations but also activity metrics/levels including but not limited to signal magnitude area signals derived from human body acceleration signals. The algorithm includes two separate stages: detecting bed-time periods (first stage) and checking the validity of the detected bed-time periods (second stage). The detection of bed-time periods is carried out by the algorithmic process by utilizing a plurality of filters that are applied to posture angle calculations and by analyzing several criteria. The validity of the detected bed-time periods is checked by the algorithmic process by determining a bed-time duration and a level of human body movements (activity metric detection and calculation).

Figure 1:
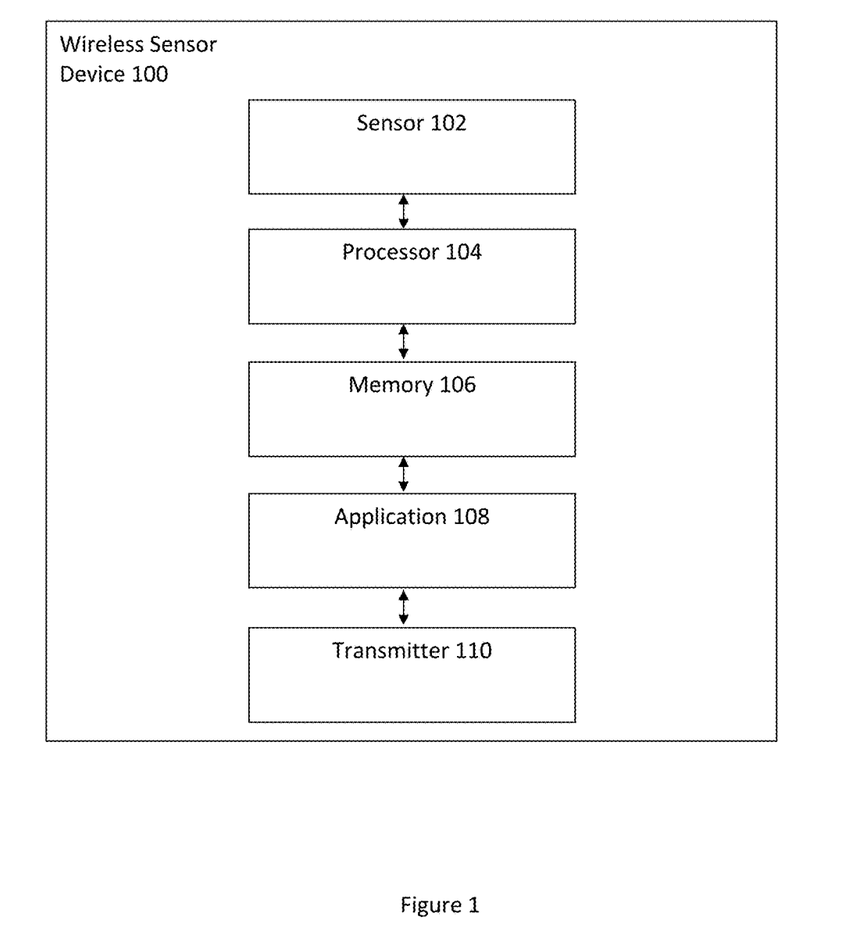
FIG. 1 illustrates a wireless sensor device for automatically determining bed-time periods in accordance with an embodiment.

FIG. 1 illustrates a wireless sensor device 100 for automatically determining bed-time periods in accordance with an embodiment. The wireless sensor device 100 ("wearable device") includes a sensor 102, a processor 104 coupled to the sensor 102, a memory 106 coupled to the processor 104, an application 108 coupled to the memory 106, and a transmitter 110 coupled to the application 108. One of ordinary skill in the art readily recognizes that the wireless sensor device 10 can include other components and that the components of the wireless sensor device 100 can be coupled in a variety of different ways and that would be within the spirit and scope of the present invention.

In one embodiment, the wireless sensor device 100 is attached to a user to detect various physiological signals via the sensor 102. The sensor 102 obtains data from the user, which is transmitted to the memory 106 and in turn to the application 108 via the processor 104. The processor 104 executes the application 108 to process and analyze the data to obtain information such as posture angles and activity metrics which are then utilized to automatically detect the bed-time events (e.g., bed-entry and bed-exit) and to determine the bed-time periods. The information is transmitted to the transmitter 110 and in turn relayed to another user or device for further processing, analysis, and storage. In another embodiment, the transmitter 110 transmits the various detected physiological signals in raw form to a remote device/server (e.g., smartphone, cloud-based server, etc.) for further processing, analysis, and storage.

In one embodiment, the sensor 102 is any of a microelectromechanical system (MEMS) multi-axial (e.g., tri-axial) accelerometer and an embedded sensor with electrodes and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention.

Additionally, one of ordinary skill in the art readily recognizes that a variety of wireless sensor devices can be utilized including but not limited to wearable devices, a wireless sensor device in a patch form-factor, the Vital Connect HealthPatch® wearable device, electrocardiograph devices, smart watches, tri-axial accelerometers, uni-axial accelerometers, bi-axial accelerometers, gyroscopes, and pressure sensors and that would be within the spirit and scope of the present invention.

In one embodiment, the HealthPatch® wearable device is a disposable adhesive patch biosensor worn on the chest that incorporates two surface electrodes with hydrogel on the bottom, a battery, an electronic module with an embedded processor and other electronic components and circuitry, a MEMS tri-axial accelerometer, and a Bluetooth Low Energy (BLE) transceiver.

In one embodiment, the wearable device facilitates continuous and automated monitoring of a plurality of physiological signals including but not limited to posture angles and activity metrics. In this embodiment, after the wearable device detects the plurality of physiological signals via a plurality of internal and embedded sensors, the electronic module of the wearable device utilizes a plurality of algorithms (e.g., firmware algorithms) to process raw waveforms of the plurality of physiological signals and to transmit a stream of the processed physiological variables via the BLE transceiver/link as encrypted data to a relay such as a smartphone, where the live (real-time) streams of data can be viewed and stored.

To describe the features of the present invention in more detail, refer now to the following description in conjunction with the accompanying Figures.

The wearable device utilizes a plurality of sensors and algorithmic processes to automatically detect bed-time events including but not limited to bed-entry and bed-exit events of a user. One of the algorithmic processes verifies the validity of detected bed-time events based on a plurality of sensors, timing (such as day-time or night-time), and time duration. In one embodiment, the plurality of algorithmic processes includes a first algorithmic process and a second algorithmic process.

Figure 2:
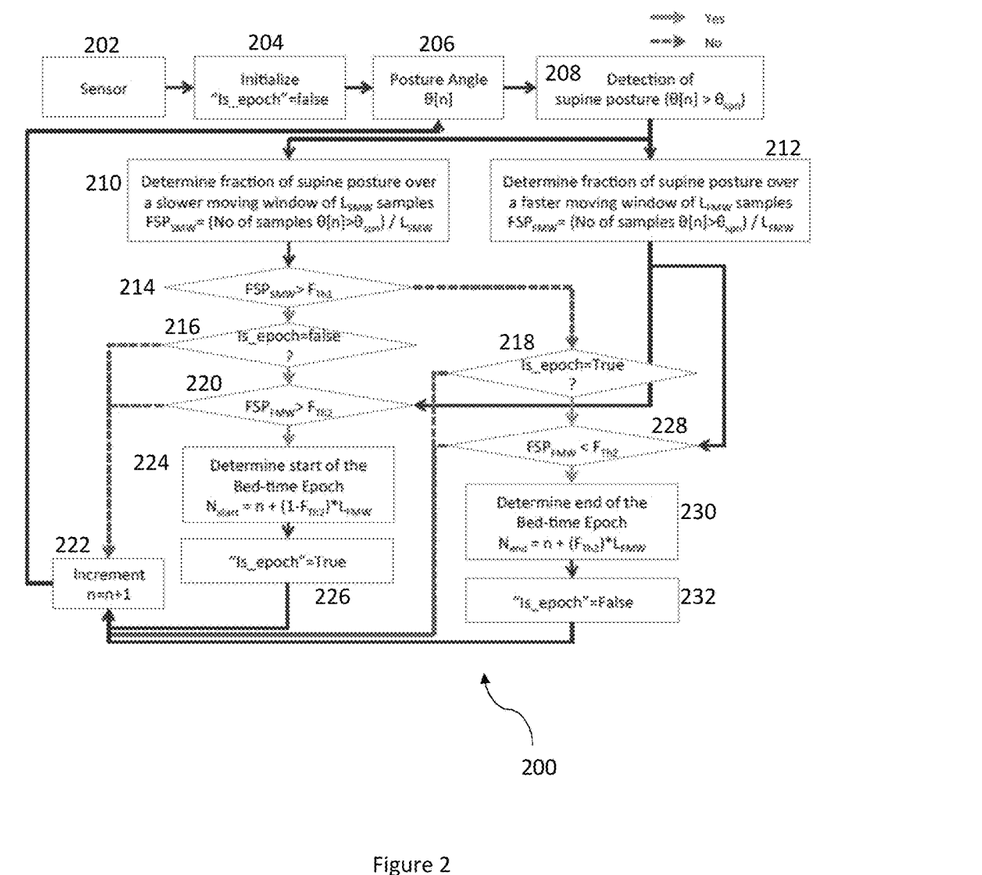
FIG. 2 illustrates a detailed flowchart of a method for automatically determining bed-time periods in accordance with an embodiment.

FIG. 2 illustrates a detailed flowchart of a method 200 for automatically determining bed-time periods in accordance with an embodiment. Each bed-time period represents the time the person is in bed (or the difference in time between when the person enters bed, or bed-entry event, and when the person exits bed, or bed-exit event). The method 200 includes utilizing a sensor that measures a plurality of physiological signals, including uniaxial/biaxial/triaxial acceleration signals, via step 202. A variable ("Is_epoch")

denoting whether a bed-time epoch is onset or offset is initialized as false, via step 204. The variable "Is_epoch" is a logical variable that takes a value of either 1 or 0 for onset/offset respectively. Before detecting the onset (entering bed-time), the variable is a value of 0. Once the onset is detected, the variable is a value of 1 according to the plurality of algorithmic processes. The state of the "Is_epoch" variable helps to detect the offset or when the bed-time terminates.

In one embodiment, an algorithmic process of the wearable device is utilized to detect the plurality of physiological signals and carry out the steps of the method 200. The method 200 includes determining a posture angle $\theta[n]$ which is an angle of the person's body with respect to gravity, via step 206, and detecting a supine posture when $\theta[n] > \theta_{spn}$, via step 208, where $\theta_{spn}$ is a threshold that detects the supine condition.

In one embodiment, the posture angle $\theta[n]$ is the arc cosine of the negative acceleration in the y direction $A_y(n)$, normalized by the gravity vector g as $\theta[n]=\cos^{-1}(-A_y[n]/g)$, where n is the sample number. The theta angle $\theta[n]$ determines various postures of the human body that is attached with the wearable device on a location, including but not limited to the user's chest. For example, a standing upright posture may have a theta angle close to 0°, and a supine or a lying down posture may have a theta angle close to 90°. $\theta_{spn}$ is an arbitrary threshold (e.g., $\theta_{spn}=40$) that detects the transition from no supine to supine posture conditions.

For a given sample number n and a respective determined posture angle $\theta[n]$, the detection of a supine posture is defined as a logical value "1" according to the relation $\theta[n] > \theta_{spn}$, otherwise as "0". The resulting logical output is fed to two moving windows of different length ($L_{SMW}$ and $L_{FMW}$) simultaneously that act as low-pass filters, and a fraction of the supine posture (FSP) is calculated. $L_{SMW}$ and $L_{FMW}$ are a predetermined number of the samples in a slower moving window (SMW) and in a faster moving window (FMW), respectively. For example, the $L_{SMW}$ can be predetermined to be 1800×fs and the $L_{FMW}$ can be predetermined to be 10×fs, where fs is the sampling rate of the posture angle $\theta[n]$.

Based upon the predeterminations of $L_{SMW}$ and $L_{FMW}$, the method 200 determines a fraction of the supine posture (FSP) over a slower moving window ($FSP_{SMW}$) of $L_{SMW}$ samples per the following equation (1): $FSP_{SMW}$=(Number of Samples when $\theta[n] > \theta_{spn}$)/$L_{SMW}$, via step 210, and determines a fraction of the supine posture (FSP) over a faster moving window (FSPFMW) of $L_{FMW}$ samples per the following equation (2): FSPFMW=(Number of Samples when $\theta[n] > \theta_{spn}$)/$L_{FMW}$, via step 212.

After determining the fraction of the supine posture via steps 210 and 212, the method 200 first determines whether $FSP_{SMW}$ is greater than a predefined or predetermined fraction threshold ($F_{Th1}$), via step 214. The fraction threshold $F_{Th1}$ is an arbitrary threshold (e.g., $F_{Th1}=0.8$) that corresponds to a slow moving window fraction of supine. If $FSP_{SMW}$ is greater than $F_{Th1}$, the method 200 determines whether Is_epoch is previously set to be false, via step 216. If yes (the Is_epoch variable is previously set to be false), this indicates that the bed-time epoch has yet to be onset, and the method 200 determines whether the fraction of the supine posture over a faster moving window (FSPFMW) per equation (2) is greater than a second predetermined fraction threshold $F_{Th2}$ (e.g., $F_{Th2}=0.9$), via step 220.

If the FSPFMW is determined to be greater than the second threshold ($FSP_{FMW} > F_{Th2}$) via step 220, the method 200 determines the start of the bed-time epoch ($N_{start}$) per the following equation (3): $N_{start}=n+(1-F_{Th2})*L_{FMW}$, via step 224. As a bed-time epoch is onset via step 224, the variable "Is_epoch" is changed from false to true (e.g., 0 to 1), via step 226. The method 200 then increments the sample number (n=n+1) of the posture angle $\theta[n]$, via step 222, and returns back to the posture angle determination of step 206 to determine the posture angle of $\theta[n+1]$ and to perform the subsequent steps of the method 200 for the current sample number.

On the other hand, if the $FSP_{SMW}$ is determined to be less than or equal to the first threshold ($FSP_{SMW} <= F_{Th1}$) thereby not satisfying the step 214, the method 200 determines whether Is_epoch=true, via step 218. If the bed-time epoch is already onset (i.e., Is_epoch=true), the method 200 checks whether the $FSP_{FMW}$ is less than $F_{Th2}$ ($FSP_{FMW} < F_{Th2}$), via step 228. If this condition is satisfied, the current bed-time epoch is to be terminated (bed-time epoch ends). The method 200 determines the end of the bed-time epoch ($N_{end}$) per the following equation (4): $N_{end}=n+(F_{Th2})*L_{FMW}$, via step 230. As a bed-time epoch is offset via step 230, the variable "Is_epoch" is changed from true to false (e.g., 1 to 0), via step 232. The method 200 then increments the sample number (n=n+1) of the posture angle $\theta[n]$, via step 222, and returns back to the posture angle determination of step 206 to determine the posture angle of $\theta[n+1]$ and to perform the subsequent steps of the method 200 for the current sample number.

The onset of bed-time is detected only when the three conditions ($FSP_{SMW} > F_{Th1}$), (Is_epoch=False?) and ($FSP_{FMW} > F_{Th2}$) via steps 214, 216 and 220, respectively are satisfied. On the other hand, the offset of bed-time is detected only when the condition ($FSP_{SMW} > F_{Th1}$) of step 214 is not satisfied, and the conditions (Is_epoch=True?) and ($FSP_{FMW} > F_{Th2}$) of steps 218 and 228, respectively are satisfied. In this process, if any of the conditions of steps 216, 218, 220, 228 are not satisfied, the method 200 increments the sample number (n=n+1) of the posture angle $\theta[n]$, via step 222, and returns back to the posture angle determination of step 206 to determine the posture angle of $\theta[n+1]$ and to perform the subsequent steps of the method 200 for the current sample number.

$N_{start}$ and $N_{end}$ are the sample numbers of the start and end of a detected bedtime epoch and the time duration between the $N_{start}$ and $N_{end}$ samples represents the bedtime period. The method 200 automatically detects a plurality of $N_{start}$ (bed-entry) and $N_{end}$ (bed-exit) time events and automatically determines the plurality of bed-time periods.

The bed-time periods that are determined utilizing posture angles alone can produce potential false positives or false negatives due to inherent limitations of changes in the posture angle value. Certain factors, including but not limited to unusual sleeping postures, tosses and turns, sleeping with too many pillow supports, and human body types, may primarily cause false negatives or false negative epochs (resulting in an actual bed-time period being identified as an awake period or a not confined to bed period). Prolonged durations of an unknown posture (e.g., lying on an inclined couch) may lead to false positives or false positive epochs (resulting in a period of not confined to bed being identified as a bed-time period).

Therefore, in another embodiment, an additional algorithmic process utilizes an activity metric/level (e.g., signal magnitude area or SMA) along with the time durations of the detected bed-time epochs to evaluate the validity of the detected bed-time epochs that leads to the elimination/rejection of potential false positive epochs and convert the potential false negative duration into the true positive bedtime period. A false positive is a time period when the subject may not be bed confined. Therefore, eliminating false positives increases the accuracy of the bed-time detection. On the other hand, a false negative is like identifying when the subject is bed confined and so converting false negatives into true positives increases the accuracy.

Figure 3:
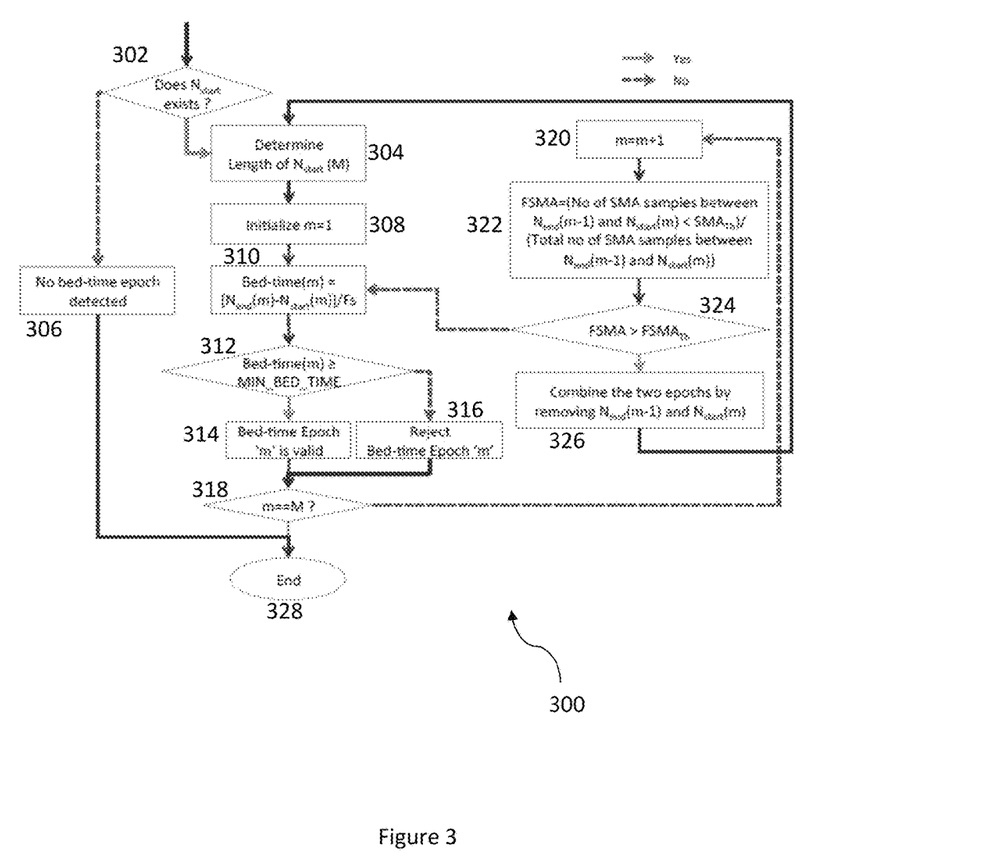
FIG. 3 illustrates a detailed flowchart of a method for automatically determining the validity of detected bed-time periods in accordance with an embodiment.

FIG. 3 illustrates a detailed flowchart of a method 300 for automatically determining the validity of detected bed-time periods in accordance with an embodiment. The method 300 is an extension of the method 200 that represents a second stage of the overall algorithmic process that the wearable device utilizes to automatically detect bed-time periods. Therefore, the method 200 can be represented as the first stage of the algorithmic process and the method 300 can be represented as the second stage of the algorithmic process. One of ordinary skill in the art readily recognizes that the wearable device may utilize only the first stage (or method 200) to determine the bed-time periods of the user of the wearable device. The second stage method 300 verifies the detection process and improves the accuracy of the detection by determining whether a couple of conditions are met.

In FIG. 3, the method 300 initially determines whether the first stage of the algorithm has detected a bed-time period by checking if the variable $N_{start}$ exists or has been previously determined (by step 224 of the aforementioned method 200), via step 302. If $N_{start}$ does not exist, the method 300 determines that no bed-time epoch has been detected, via step 306. In this case, the verification process of the method 300 is not required and the algorithmic process is terminated, via step 328.

If $N_{start}$ does exit, the method 300 determines the length of $N_{start}$ as M, via step 306, since there could be more than one bed-time epoch. M represents the number of bed-time period epochs and $N_{start}$ corresponds to the sample number for the start of bed-time epoch previously determined by the method 200. The method 300 initializes the epoch loop number m as m=1, via step 308. For example, if the method 200 determines three $N_{start}$ and three $N_{end}$ values, then the method 200 also calculates three bed-time periods as a time difference between the respective $N_{end}$ and $N_{start}$ sample numbers. Therefore, the number of bed-time period epochs (or M) is also determined to be three.

The method 300 determines bed-time duration of the $m^{th}$ epoch per the following equation (5): bed-time(m)=[$N_{end}$(m)-$N_{start}$(m)]/Fs, via step 310, where the $N_{start}$ and $N_{end}$ values are the sample numbers determined by the method 200, m is the epoch number, and Fs is a sampling frequency. After determining the bed-time(m) via step 310, the method 300 determines whether the bed-time(m) is greater than or equal to a threshold for a minimum duration of a bed-time period (MIN_BED_TIME), via step 312. In one embodiment, MIN_BED_TIME is one hour.

If the determined bed-time period is longer than the minimum duration of a bed-time period (minimum bed-time period) (bed-time(m)>=MIN_BED_TIME), the method 300 determines that the bed-time epoch 'm' as valid, via step 314. If the determined bed-time period is less than the minimum bed-time period (bed-time(m)<MIN_BED_TIME), the method 300 rejects the bed-time epoch 'm'', via step 316 that eliminates the $N_{start}$(m) and $N_{end}$(m). After verifying the validity of the bed-time epoch 'm' either by accepting or rejecting the bed-time epoch 'm' per steps 314 and 316, the method 300 determines whether all the bed-time epochs are verified by checking whether the current epoch number m is equal to the total number of detected epochs M (e.g., m=M?), via step 318. If all the detected bed-time epochs are verified, the algorithmic process of the method 300 is terminated, via step 328.

On the other hand, if all the detected bed-time epochs are not verified yet (e.g., (m#M), then the method 300 increments the loop number (m=m+1), via step 320, and considers the next bed-time epoch for analysis to determine the activity level between the start time of the current epoch and the end time of the previous epoch as the fraction of the signal magnitude area (FSMA) per the following equation (6): FSMA=(Number of SMA samples between $N_{end}$(m-1) and $N_{start}$(m)<$SMA_{Th}$/(Total number of SMA samples between $N_{end}$(m-1) and $N_{start}$(m), via step 322. The FSMA represents the likelihood of the user being in an inactive state as determined by the SMA threshold $SMA_{Th}$.

Once the FSMA is determined via step 322, the method 300 determines whether the FSMA is greater than a threshold for the FSMA ($FMSA_{Th}$), via step 324. $FMSA_{Th}$ is an arbitrary threshold (e.g., $FMSA_{Th}$=0.90) representing the likelihood of being inactive. If the fraction of SMA does not satisfy the inactivity criteria (e.g., FSMA<=$FSMA_{Th}$), the method 300 repeats the steps 310, 312, 314,316, 318 for the current bed-time epoch m and evaluates the validity of the epoch by comparing the determined time duration of the current epoch to the minimum bed-time period. The method 300 then determines whether all of the bed-time epochs are verified by checking whether the current epoch number m is equal to the total number of detected epochs M (e.g., m=M?), via step 318. If all of the detected bed-time epochs are verified, the algorithmic process of the method 300 is terminated, via step 328, otherwise the method 300 increments the loop number (m=m+1), via step 320, and repeats the steps of the method 300 to check the validity of each epoch based on a SMA level and a minimum bed-time duration.

On the other hand, if the fraction of SMA satisfies the inactivity criteria (FSMA>$FSMA_{Th}$), the method 300 combines the current and previous epochs by eliminating $N_{end}$(m-1) and $N_{start}$(m), via step 326. Once the two epochs are combined via step 326 (which converts the false negative bed-time period into a true positive bed-time period and merges with both the current and the previous true positive bed-time periods), the method 300 returns back to step 304 to repeat the processes that determine the length of $N_{start}$ as M thereby carrying out the subsequent steps of the method 300.

Figure 4:
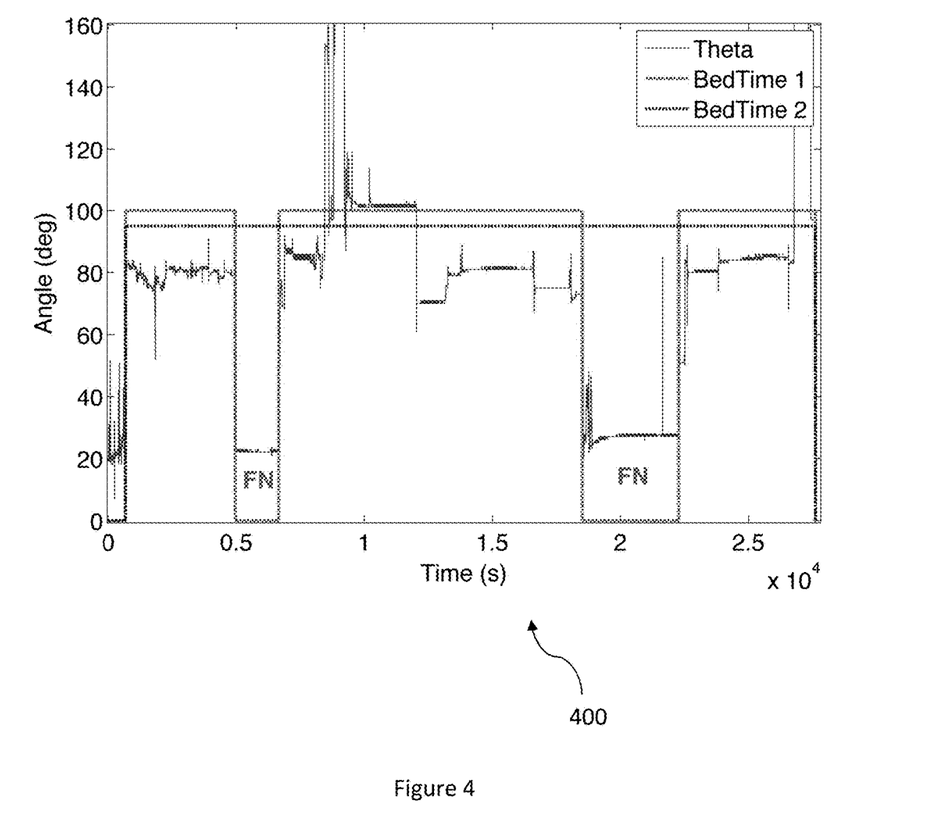
FIG. 4 illustrates a diagram that compares the determinations of bed-time periods using posture angles alone in accordance with a first embodiment and using both posture angles and activity metrics in accordance with a second embodiment.

FIG. 4 illustrates a diagram 400 that compares the determinations of bed-time periods using posture angles alone (denoted as 'BedTime 1' with '--') in accordance with a first embodiment, and using both posture angles and activity metrics (denoted as 'BedTime 2' with '-.-') in accordance with a second embodiment. The diagram 400 plots time in seconds versus angle in degrees (denoted with '-'). As the diagram 400 depicts, the first embodiment utilizes only the posture angles to detect the bed-time periods which produces two false negative bed-time periods labeled as 'FN' (around the time points of 6,000 and 20,000 seconds) that also splits a single true positive bed-time epoch into three positive segments that produces two more false bed-entries and bed-exits. On the other hand, the bed-time period determined by the second embodiment utilizes an algorithmic process that integrates the posture angle, a minimum bed-time period, and activity metric analysis to eliminate the false negative bed-time periods and to provide a more accurate and automated bed-time period determination. In one embodiment, the minimum bed-time period is predetermined or is learned from a clinical trial data.

Figure 5:
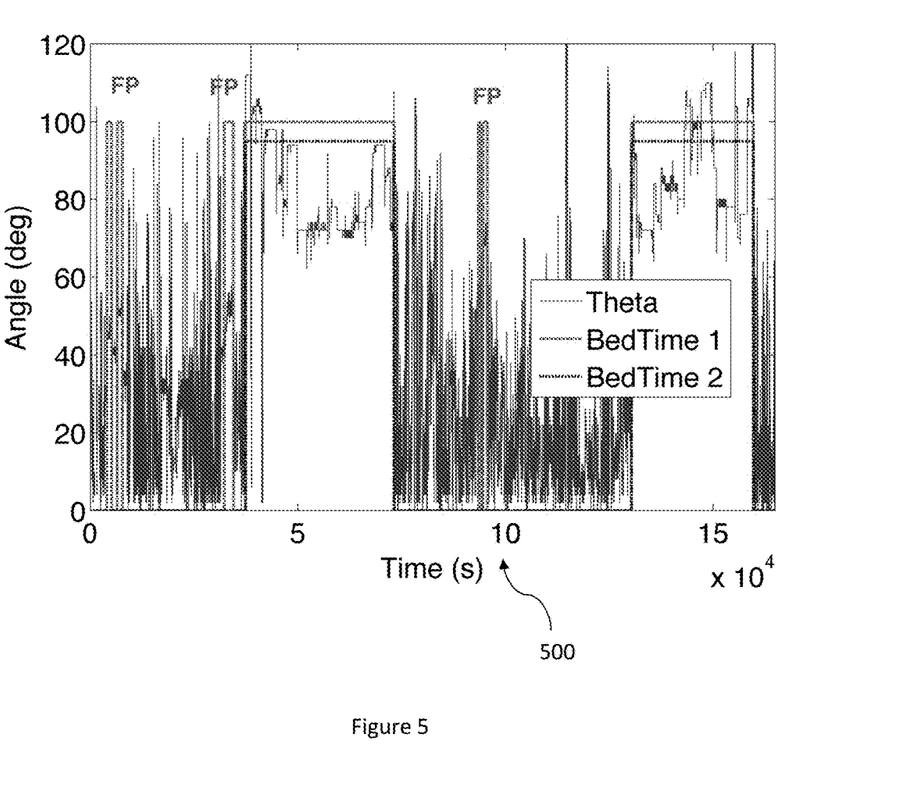
FIG. 5 illustrates a diagram that compares the determinations of bed-time periods for two consecutive days of data using posture angles alone in accordance with a first embodiment and using both posture angles and activity metrics in accordance with a second embodiment.

FIG. 5 illustrates a diagram 500 that compares the determinations of bed-time periods for two consecutive days of data using posture angles alone (denoted as 'BedTime 1' with '--') in accordance with a first embodiment, and using both posture angles and activity metrics (denoted as 'BedTime 2' with '-.-') in accordance with a second embodiment. The diagram 500 plots time in seconds versus angle in degrees (denoted with '-'). As the diagram 500 depicts, the first embodiment utilizes only the posture angles which produces five false positive bed-time periods labeled as 'FP' thereby producing five false bed-entry and five false bed-exit events. On the other hand, the bed-time period determined by the second embodiment utilizes an algorithmic process that integrates the posture angle, a minimum bed-time period, and activity metric analysis to eliminate the false positive bed-time periods and to provide a more accurate and automated bed-time period determination.

Figure 6:
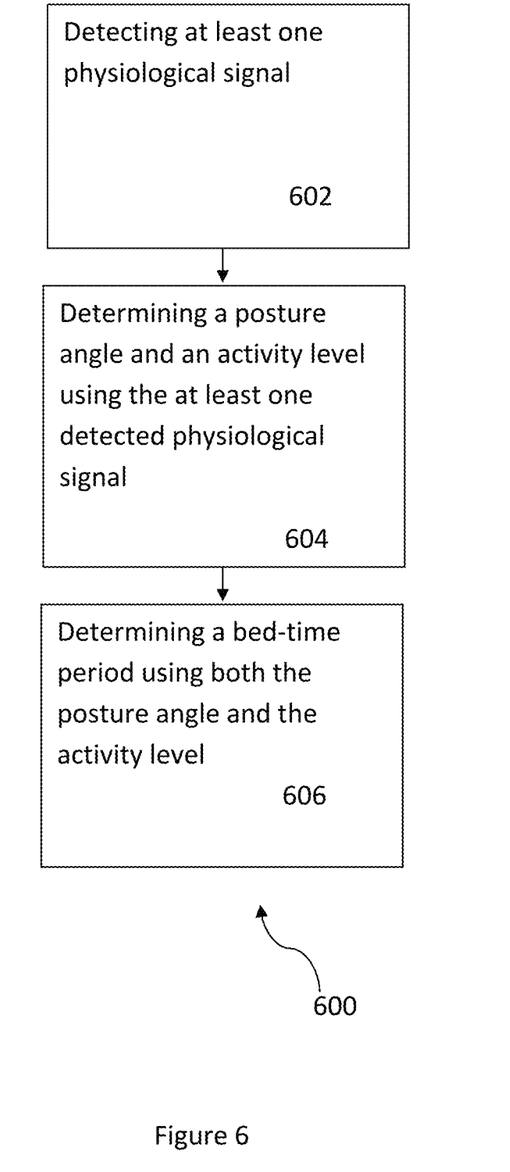
FIG. 6 illustrates a method for automatically determining bed-time periods in accordance with an embodiment.

FIG. 6 illustrates a method 600 for automatically determining bed-time periods in accordance with an embodiment. The method 600 comprises detecting at least one physiological signal, via step 602, determining a posture angle and an activity level using the at least one detected physiological signal, via step 604, and determining a bed-time period using the posture angle and the activity level, via step 606. In one embodiment, a wearable device determines the bed-time period of a user using only the posture angle. In another embodiment, the wearable device determines the bed-time period using both the posture angle and the activity level. In one embodiment, the at least one detected physiological signal is at least one acceleration signal of the user (human body).

In one embodiment, the detecting the posture step further comprises calculating a posture angle during the at least one acceleration signal and determining whether the posture angle is greater than a supine posture threshold. The supine posture threshold can be any of a predetermined threshold value or a threshold value learned from a data sampling including but not limited to clinical studies. In one embodiment, the determining the bed-time period further comprises determining a bed-entry event and determining a bed-exit event, wherein the bed-time period is a time difference between the bed-entry event and the bed-exit event.

In one embodiment, the determining of the bed-entry event further comprises determining a fraction/likelihood of supine posture over two time windows of different lengths (a slower time window and a faster time window). If the fraction of the supine posture exceeds two predetermined thresholds ($F_{Th1}$ and $F_{Th2}$), one ($F_{Th1}$) for the slower time window and the other ($F_{Th2}$) for the faster time window respectively, then the bed-entry event or the start of the bed-time period has been determined. In one embodiment, the fraction of the supine posture over a slower moving window ($FSP_{SMW}$) is determined as a number of samples during the supine posture (when $\theta[n] > \theta_{spn}$) divided by a slower moving window of samples ($L_{SMW}$) and the fraction of the supine posture over a faster moving window ($FSP_{FMW}$) is determined as a number of samples during the supine posture (when $\theta[n] > \theta_{spn}$) divided by a faster moving window of samples ($L_{FMW}$).

Therefore, in this embodiment, the determining of the bed-entry event comprises determining whether a fraction of the supine posture over a slower moving window ($FSP_{SMW}$) is greater than a first threshold; and in response to the $FSP_{SMW}$ being greater than the first threshold, determining whether a fraction of the supine posture over a faster moving window ($FSP_{FMW}$) is also greater than a second threshold; if both $FSP_{SMW}$ is greater than the first threshold and $FSP_{FMW}$ is greater than the second threshold, the bed-entry event is determined for the given data sample number.

In this embodiment, if the two conditions (first condition—$FSP_{SMW}$ greater than the first threshold $F_{Th1}$ and second condition—$FSP_{FMW}$ greater than the second threshold $F_{Th2}$) are satisfied, then the bed-entry event is detected/determined by the wearable device. The time instance of the bed-entry is determined using the sample number n that satisfies both the two aforementioned conditions ($FSP_{SMW} > F_{Th1}$ and $FSP_{FMW} > F_{Th2}$) per the following equation: $N_{start} = n + (1 - F_{Th2}) * L_{FMW}$.

In one embodiment, the determining of the bed-exit event further comprises determining when the fraction of supine posture is less than the predetermined thresholds ($F_{Th1}$ and $F_{Th2}$) for both the slower time window and the faster time window respectively. In this embodiment, if the two conditions (first condition—$FSP_{SMW}$ is less than the first threshold $F_{Th1}$ and second condition—$FSP_{FMW}$ is less than the second threshold $F_{Th2}$) are satisfied, then the bed-exit event is detected/determined by the wearable device. The time instance of the bed-exit is determined using the sample number n that satisfies both of the two aforementioned conditions ($FSP_{SMW} < F_{Th1}$ and $FSP_{FMW} < F_{Th2}$) per the following equation: $N_{end} + n + (F_{Th2}) * L_{FMW}$.

Therefore, in this embodiment, the determining of the bed-exit event comprises in response to the $FSP_{SMW}$ being less than or equal to the first threshold, determining whether a fraction of the supine posture over a faster moving window ($FSP_{FMW}$) is less than the second threshold; if $FSP_{SMW}$ is less than or equal to the first threshold and $FSP_{FMW}$ is less than the second threshold, the bed-exit event is determined for the given data sample number.

In another embodiment, the at least one physiological signal includes at least one acceleration signal of the user's body (human body) and a posture angle and an activity metric/level are derived from the at least one acceleration signal. In one embodiment, the activity metric/level is a signal magnitude area (SMA) signal derived from the at least one detected acceleration signal. In this embodiment, the method 600 further comprises validating the determination of the bed-time period using the activity level and a minimum bed-time period.

In one embodiment, a system for automatically determining bed-time periods comprises at least one sensor to detect a plurality of physiological signals, a processor coupled to the at least one sensor, and a memory device coupled to the processor, wherein the memory device includes an application that, when executed by the processor, causes the processor to detect a supine posture using at least one of the plurality of detected physiological signals and to determine a bed-time period using the detected supine posture.

In one embodiment, the plurality of physiological signals includes a posture angle and an activity metric. In one embodiment, to detect the supine posture further comprises to determine whether the posture angle is greater than a supine posture threshold. In one embodiment, to determine the bed-time period further comprises to determine a bed-entry event and to determine a bed-exit event, wherein the bed-time period is a time difference between the bed-entry event and the bed-exit event.

In one embodiment, the bed-time period is determined as the time difference between the bed-exit and bed-entry events. The calculated bed-time period is compared to a minimum bed-time period to identify a potential false positive if the calculated bed-time period is less than the minimum bed-time period. Once identified, the false positive bed-time period is rejected. False negative bed-time periods are detected based on an estimate of a fraction/likelihood of inactivity denoted as an FSMA value compared to a predetermined or learned threshold $FSMA_{Th}$. If the FSMA value is greater than the threshold $FSMA_{Th}$, then the time duration between a current bed-entry event and a previous bed-exit event is identified as a false negative and thus converted as a true positive bed-time period, as shown in FIG. 4. In one embodiment, a wearable device includes at least one sensor, a processor coupled to the at least one sensor, and a memory device coupled to the processor, wherein the memory device includes an application, that when executed by the processor, further causes the processor to validate the determination of the bed-time period using the activity level/metric and a minimum bed-time period.

As above described, a method and system in accordance with the present invention utilizes a wearable device (e.g., HealthPatch® patch sensor) to automatically detect bed-time events (including but not limited to bed-entry and bed-exit) and determine bed-time periods (or the time periods that a user of the wearable device is in bed) from those bed-time events. By utilizing a wearable device to detect/derive a plurality of physiological signals (e.g., acceleration signals, posture angles, and activity metrics) via a plurality of embedded sensors (e.g., a MEMS accelerometer, and derived sensors), and utilizing embedded algorithms and a processor (e.g., any of an embedded electronic module/processor in the wearable device, an external relay/cloud processor such as a smartphone device, and a cloud computing system) to perform an algorithmic process, the method and system continuously and automatically determine bed-time periods. In addition, by integrating an analysis of both posture angles and activity metrics into the algorithmic process, the method and system reduce false positives/negatives and provide a more accurate determination of bed-time periods.

A method and system for automatically determining bed-time periods has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium (non-transitory). Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for automatically determining bed-time periods, comprising:
   detecting, by a wearable sensor device, at least one physiological signal;
   determining, by the wearable sensor device, a posture angle and an activity level using the at least one detected physiological signal; and
   determining, by the wearable sensor device, a bed-time period using both the posture angle and the activity level, wherein the determining the bed-time period further comprises:
      determining a bed-entry event, wherein the determining of the bed-entry event further comprises:
         determining whether a fraction of the supine posture over a slower moving window (FSPSMW) is greater than a first threshold, and
         in response to the FSPSMW being greater than the first threshold, determining whether a fraction of the supine posture over a faster moving window (FSPFMW) is greater than a second threshold; and
      determining a bed-exit event, wherein the bed-time period is a time difference between the bed-exit event and the bed-entry event.

2. The method of claim 1, wherein the at least one detected physiological signal is at least one acceleration signal of a user.

3. The method of claim 2, wherein the determining the posture angle further comprises:
   determining whether the posture angle is greater than a supine posture threshold.

4. The method of claim 3, wherein the supine posture threshold is any of a predetermined threshold value and a threshold value learned from a data sampling.

5. The method of claim 4, further comprising:
   validating the determination of the bed-time period using the activity level and a minimum bed-time period.

6. The method of claim 2, wherein the activity level is a signal magnitude area (SMA) signal derived from the at least one acceleration signal.

7. The method of claim 1, wherein the FSPSMW is determined as a number of samples with the supine posture divided by a slower moving window of samples.

8. The method of claim 1, wherein the FSPFMW is determined as a number of samples with the supine posture divided by a faster moving window of samples.

9. The method of claim 1, wherein if both the FSPSMW is greater than the first threshold and the FSPFMW is greater than the second threshold, the bed-entry event is determined for a given data sample number.

10. The method of claim 1, wherein the determining of the bed-exit event further comprises:
    in response to the FSPSMW being less than or equal to the first threshold, determining whether a fraction of the supine posture over a faster moving window (FSPFMW) is less than the second threshold.

11. The method of claim 10, wherein if the FSPSMW is less than or equal to the first threshold and FSPFMW is less than the second threshold, the bed-exit event is determined as a function of the second threshold and the faster moving window of samples.

12. A system for automatically determining bed-time periods, the system comprising at least one sensor to detect a plurality of physiological signals, a processor coupled to the at least one sensor, and a memory device coupled to the processor, wherein the memory device includes an application that, when executed by the processor, causes the processor to:
   determine a posture angle and an activity level using at least one of the plurality of detected physiological signals; and
   determine a bed-time period using both the posture angle and the activity level, wherein the determining the bed-time period comprises:
      determining a bed-entry event, and
      determining a bed-exit event;
   wherein the determining the bed-entry event and the bed-exit event comprises:
      determining whether a fraction of the supine posture over a slower moving window (FSPSMW) is greater than a first threshold,
      in response to the FSPSMW being greater than the first threshold, determining whether a fraction of the supine posture over a faster moving window (FSPFMW) is greater than a second threshold, wherein if both FSPSMW is greater than the first threshold and FSPFMW is greater than the second threshold, the bed-entry event is determined for a given data sample number, and
      in response to the FSPSMW being less than or equal to the first threshold, determining whether a fraction of the supine posture over a faster moving window (FSPFMW) is less than the second threshold, wherein if FSPSMW is less than or equal to the first threshold and FSPFMW is less than the second threshold, the bed-exit event is determined for the given data sample number; and
   wherein the bed-time period is a time difference between the bed-exit event and the bed-entry event.

13. The system of claim 12, wherein the plurality of physiological signals includes at least one acceleration signal of a user, further wherein the activity level is a signal magnitude area (SMA) signal derived from the at least one acceleration signal.

14. The system of claim 13, wherein to determine the posture angle further comprises to:
   determine whether the posture angle is greater than a supine posture threshold.

15. The system of claim 12, wherein the application, when executed by the processor, further causes the processor to:
   validate the determination of the bed-time period using the activity level and a minimum bed-time period.

* * * * *